(12) United States Patent
Hansis et al.

(10) Patent No.: US 12,027,252 B2
(45) Date of Patent: Jul. 2, 2024

(54) QUALITY FEEDBACK SYSTEM FOR MEDICAL IMAGES

(71) Applicant: KONINKLIJKE PHILIPS N.V., Eindhoven (NL)

(72) Inventors: Eberhard Sebastian Hansis, Munich (DE); Falk Uhlemann, Norderstedt (DE); Thomas Netsch, Hamburg (DE); Jörn Borgert, Hamburg (DE); Michael Günter Helle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 743 days.

(21) Appl. No.: 17/258,482

(22) PCT Filed: Jul. 5, 2019

(86) PCT No.: PCT/EP2019/068179
§ 371 (c)(1),
(2) Date: Jan. 7, 2021

(87) PCT Pub. No.: WO2020/011683
PCT Pub. Date: Jan. 16, 2020

(65) Prior Publication Data
US 2021/0233644 A1    Jul. 29, 2021

Related U.S. Application Data

(60) Provisional application No. 62/695,241, filed on Jul. 9, 2018.

(51) Int. Cl.
*G16H 30/20* (2018.01)
*G16H 10/60* (2018.01)
(Continued)

(52) U.S. Cl.
CPC ............ *G16H 30/20* (2018.01); *G16H 10/60* (2018.01); *G16H 30/40* (2018.01); *G16H 40/20* (2018.01)

(58) Field of Classification Search
CPC ........ G16H 30/20; G16H 40/20; G16H 10/60; G16H 30/40
(Continued)

(56) References Cited

U.S. PATENT DOCUMENTS

2003/0110178 A1    6/2003    Woods et al.
2005/0256743 A1    11/2005   Dale
(Continued)

OTHER PUBLICATIONS

International Search Report and Written Opinion for International Application No. PCT/EP2019/068179, filed Jul. 5, 2019, 17 pages.
(Continued)

*Primary Examiner* — Michael R Neff

(57) ABSTRACT

To obtain feedback on image quality from qualified reviewers, an optically machine readable code (124) (e.g., a QR code or the like) is generated for each acquired medical image and embedded into the image. The embedded code includes information to the identity of the image, the imaging device, authorized reviewers, and authorized recipients of the feedback, as well as a link to a feedback form that can be retrieved by a communication device (38) used by an authorized user. When the embedded code is scanned by the communication device, the code is decoded and the feedback form is retrieved from a server, completed by the reviewer, and transmitted back to the authorized recipients of the feedback.

13 Claims, 5 Drawing Sheets

(51) Int. Cl.
    *G16H 30/40*    (2018.01)
    *G16H 40/20*    (2018.01)
(58) Field of Classification Search
    USPC .......................................................... 382/128
    See application file for complete search history.

(56) References Cited

U.S. PATENT DOCUMENTS

| | | | |
|---|---|---|---|
| 2014/0142979 | A1 | 5/2014 | Mitsunaga |
| 2014/0231502 | A1* | 8/2014 | Marsico ................ G06F 16/955 |
| | | | 235/375 |
| 2014/0263674 | A1 | 9/2014 | Cerveny |
| 2014/0289160 | A1* | 9/2014 | Stovall ................ G06Q 30/0282 |
| | | | 705/347 |
| 2016/0117539 | A1 | 4/2016 | Gotman et al. |
| 2016/0335479 | A1 | 11/2016 | Barlett, II et al. |
| 2019/0026504 | A1* | 1/2019 | Wang ................ G06K 19/06103 |
| 2022/0350865 | A1* | 11/2022 | Minina ................ G06F 16/215 |

OTHER PUBLICATIONS

Authors Anonymous, "Technique to Secure Viewing of a Patient Medical Image by a Third Party", ip.com, 7 pages. (Abstract).

Yang, et al., "Secure Patient Information and Privacy in Medical Imaging", Systemics, Cybernetics and Informatics, vol. 8, No. 3, 2010, pp. 63-66.

* cited by examiner

QUALITY FEEDBACK SYSTEM FOR MEDICAL IMAGES

RELATED APPLICATIONS

This application is the U.S. National Phase application under 35 U.S.C. § 371 of International Application No. PCT/EP2019/068179, filed on Jul. 5, 2019, which claims the benefit of and priority to U.S. Provisional No. 62/695,241, filed Jul. 9, 2018, which is incorporated by referenced in tis entirety.

FIELD

The following relates generally to systems and methods for coding medical images to facilitate rapid image quality feedback.

BACKGROUND

Radiological images are conventionally ordered by a referring physician, acquired by a technologist and read by a radiologist. However, conventional techniques do not allow the radiologist and the referring physician to give feedback on the quality of an image, which would be valuable to the acquiring technologist or radiology department (for improving acquisition procedures) and to the manufacturer of the imaging or viewing device (to improve the device). Moreover, there is no simple and generally available feedback channel from the radiologist or referring physician.

The following discloses certain improvements.

SUMMARY

In one disclosed aspect, a system that facilitates determining medical image quality via a unique coding embedded in a medical image comprises a medical imaging device configured to acquire an image of a patient, and a coding device comprising a code generator configured to generate a machine-readable unique code for an acquired image, wherein the unique code identifies the imaging device that acquired the image, at least one party authorized to review the acquired image, and at least one communication link for accessing at least one feedback form related to the acquired image. The coding device further comprises an embedding component configured to associate the unique code with the acquired image such that the associated code is decodable when scanned, and a gray level adjustment module configured to adjust a gray level of the associated code to correspond to a gray level of the acquired image.

In another disclosed aspect, a system for providing feedback indicative of image quality for an acquired medical image comprises a server comprising a database of coded medical images, wherein each coded image comprises a machine-readable unique code including information related to an identity of a medical imaging device that acquired the coded image, an identity of at least one party authorized to review the coded image, and a link to at least one feedback form into which image quality feedback can be entered. The system further comprises a communication device comprising a scanner configured to scan the machine-readable unique code, and a processor that executes a feedback application configured to decode the scanned code, retrieve the at least one feedback form from the server via the link, present the retrieved feedback form to a reviewer for completion, and transmit the completed feedback form to the server.

In another disclosed aspect, a method of determining medical image quality via a unique coding embedded in a medical image comprises acquiring an image of region of interest in a patient via a medical imaging device, and generating a machine-readable unique code for an acquired image, wherein the unique code identifies the imaging device that acquired the image, at least one party authorized to review the acquired image, and at least one communication link for accessing at least one feedback form related to the acquired image. The method further comprises associating the unique code with the acquired image such that the associated code is decodable when scanned, and adjusting a gray level of the associated code to correspond to a gray level of the acquired image.

In another disclosed aspect a method for providing feedback indicative of image quality for an acquired medical image comprises scanning a machine readable unique code in a coded medical image, decoding the scanned code, retrieving at least one feedback form from the server via the link, presenting the retrieved feedback form to a reviewer for completion, and transmitting the completed feedback form to the server. The machine readable unique code comprises information related to an identity of a medical imaging device that acquired the coded image, an identity of at least one party authorized to review the coded image, and a link to at least one feedback form into which image quality feedback can be entered.

One advantage resides in improving image quality review by authorized personnel.

Another advantage resides in improving faulty imaging device detection.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the various described embodiments and are not to be construed as limiting the invention.

DETAILED DESCRIPTION

Figure 1:
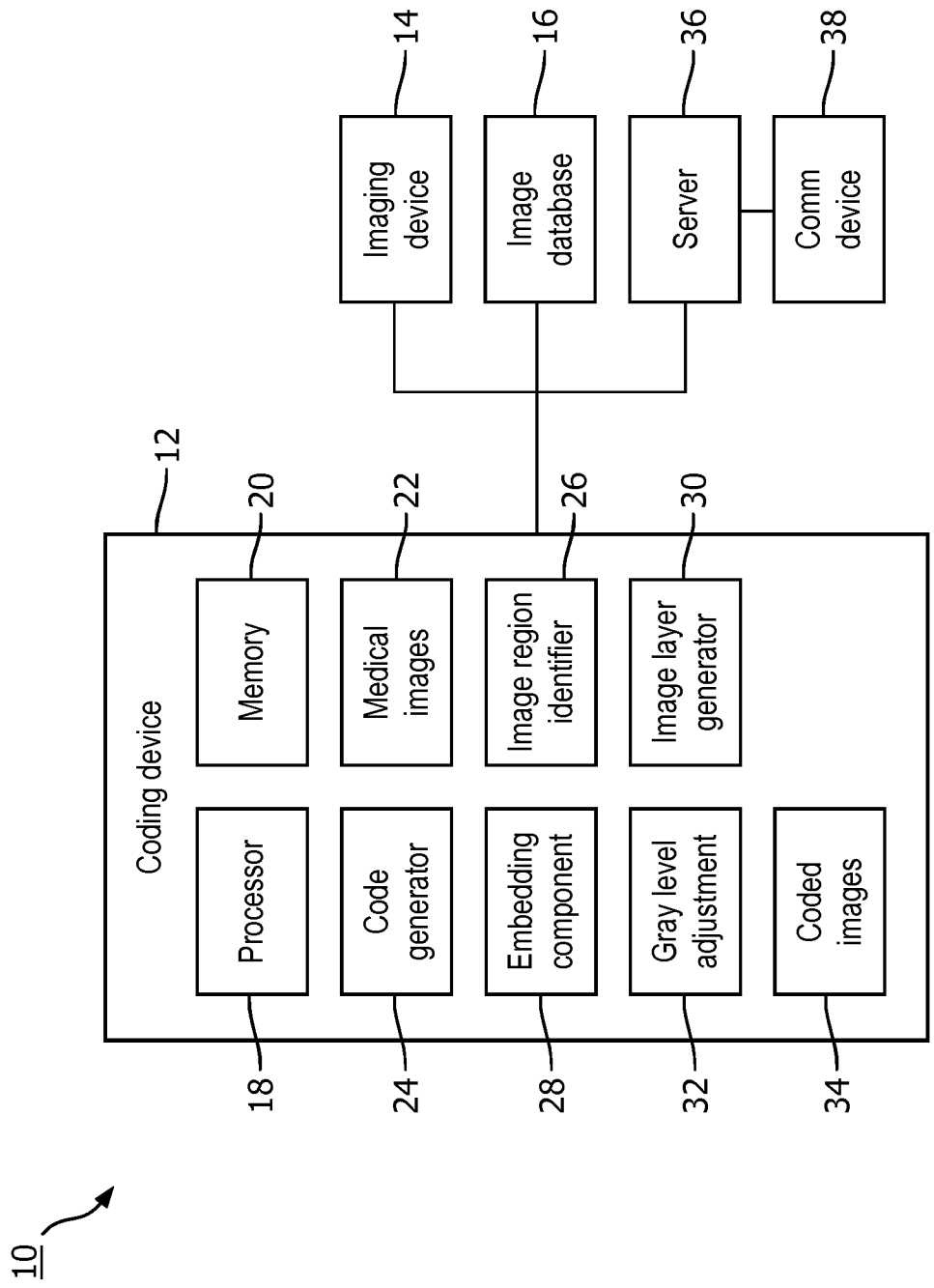
FIG. 1 illustrates a system that facilitates permitting reviewers of medical images to quickly and easily give feedback on the quality (and diagnostic usability) of a medical image, in accordance with various aspects described herein.

FIG. 1 illustrates a system that facilitates permitting reviewers of medical images to quickly and easily give feedback on the quality (and diagnostic usability) of a medical image, irrespective of the platform on which the image is being viewed and of the network connection available on the viewing platform, in accordance with various aspects described herein. The system comprises a coding device 12 configured to embed a machine-readable coding (e.g., a quick response (QR) code, bar code, or some other machine-readable coding) that can be read by a scanning device and provides information that permits an image reviewer to provide feedback on one or more qualities of the image being reviewed.

The coding device 12 is coupled to an imaging device 14 and an image database 16. In one embodiment, one or both of the image database and the coding device are integral to the imaging device. The imaging device may be, for instance, a medical imaging device such as an x-ray device, a computed tomography (CT) device, a magnetic resonance imaging (MRI) device, a positron emission tomography (PET) device, a single-photon emission computed tomography (SPECT) device, or any other suitable imaging device. In another embodiment, the imaging device is a multi-modal imaging device that combines two or more of the foregoing imaging capabilities.

The coding module further comprises a processor 18 that executes, and a memory or computer-readable medium 20 that stores, computer-executable instructions for performing the various functions, actions, routines, programs, applications, etc. described herein. The memory 20 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, flash memory, solid state memory, or any other tangible medium from which the processor 18 can read and execute. In this context, the described systems may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

The coding device 12 receives medical images 22 from the imaging device 14 and/or the image database 16, and is configured to embed a machine-readable code, such as a QR code or a watermark or the like, into each medical image. The embedded code can comprise information about the imaging device used to generate the image, acquisition parameters used during image acquisition, as well as a unique identifier for the image. In one embodiment, the embedded code is configured to omit personal, medical and/or patient information.

An image region identifier module 26 is configured to identify regions of the image for placement of the unique coding so as not to obstruct the subject of the image. The image region identifier module identifies candidate areas or regions of the image and selects one of the candidate regions that does not contain diagnostically relevant information (e.g., such as an image region depicting air outside the patient, outside of the region of interest). This can be achieved using, e.g., automatic segmentation of the patient outline. In one embodiment, when embedding the unique code the image region identifier module 26 automatically determines diagnostically relevant areas of the image (e.g. based on automatic detection of organs linked to the scan request), such as areas within a region of interest (ROI) of the patient, and an embedding module 28 embeds the unique code where it is most likely to be seen during review. Although various described embodiments refer to a QR code, any other optically machine-readable code cable of representing readable information can be used.

In another embodiment, an image layer generation module 30 generates an additional image layer into which the unique coding is embedded by the embedding component. The additional image layer can be switched on or off for viewing by the reviewer of the image, or can be presented in separate series or snapshots in the dataset. To this end, the image layer generator module 30 inserts or appends additional image layer data comprising the unique code into the image data in order to cause the image layer comprising the unique coding to be overlaid onto the image or to otherwise be presented after the reviewer views the image. During review, the reviewer of the image toggles the additional image layer on or off (e.g., on to view or scan the embedded coding, or off to view the unimpeded image), or selects an icon to view the appended unique coding.

The coding device 12 further comprises a gray level adjustment module 32 that executes a gray level adjustment to the pixel values of the unique coding (e.g., prior to embedding) or to the pixel values of the embedded coding (e.g., after embedding), such that the gray level values of the embedded code are set according to the gray level values of the diagnostically relevant image features. In this manner, the embedded coding is easily readable in default level/window settings for the main diagnostic purpose because the gray levels of the embedded code do not substantially alter the overall image histogram (e.g. do not introduce very large values). The latter feature facilitates permitting automatic image analysis methods to be able easily to process the image with the embedded code without interference form the code image.

Coded images 34, once generated by the coding device in the manner described herein are transmitted to one or more servers 36 for storage and access by a reviewer. A reviewer viewing a given coded image employs a communication device 38 (e.g., a smartphone, tablet, laptop, or the like) to scan the embedded code in the image being reviewed. The communication device decodes the embedded code to read the information included therein, retrieve a feedback form for the image under review as identified in the decoded information in order to permit the reviewer to provide feedback to a server regarding image quality. A reviewer views the image under review on any suitable device (e.g., a workstation user interface or the like), and provides feedback regarding image quality into the retrieved feedback form, which, once complete, is transmitted via a data link of the communication device to one or more servers 36.

Figure 2:
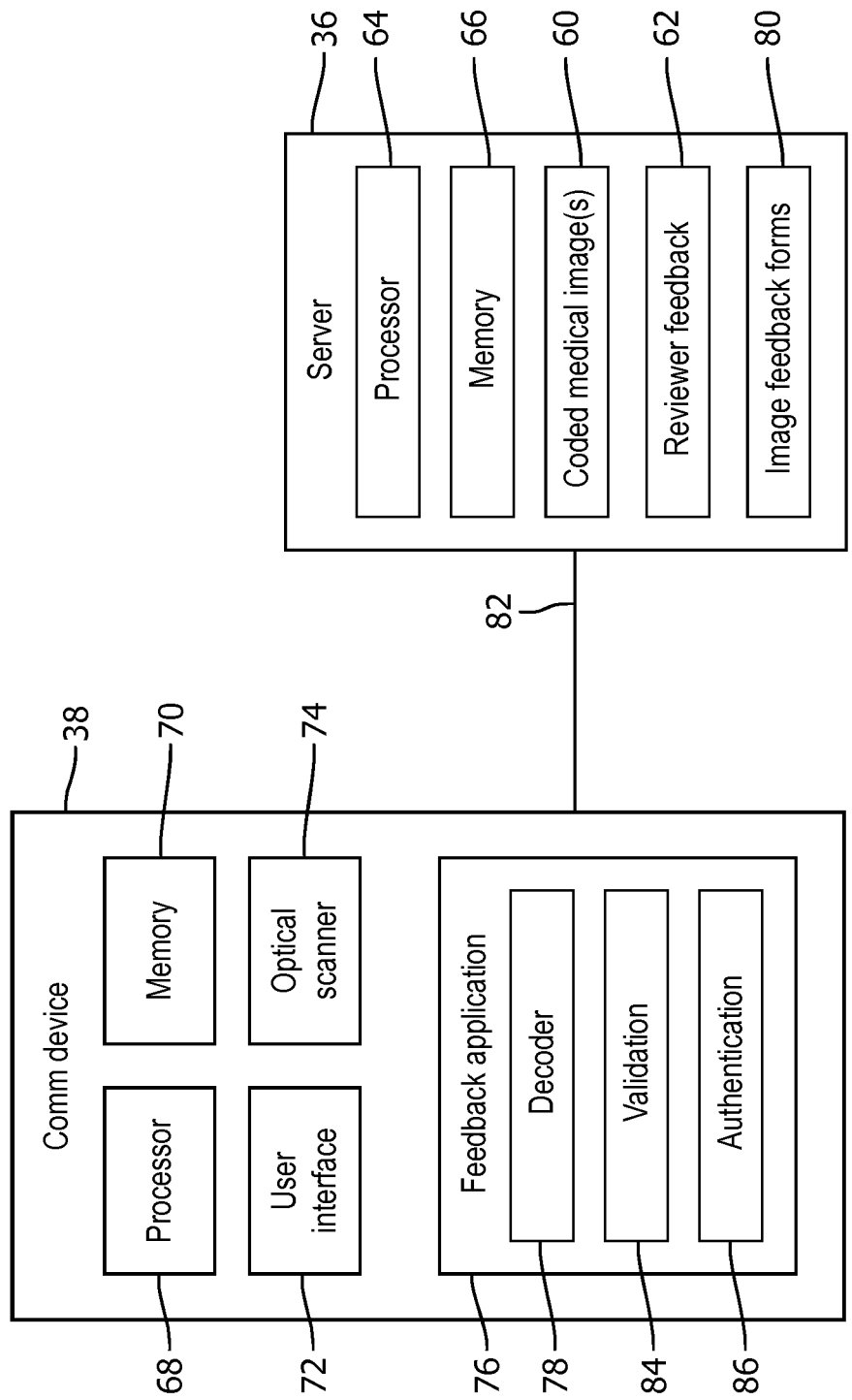
FIG. 2 illustrates in greater detail the communication device, which interacts with the server on which are stored a plurality of coded medical images.

FIG. 2 illustrates in greater detail the communication device 38, which interacts with the server 36 on which are stored a plurality of coded medical images 60, each having embedded therein or appended thereto a unique code as described above with regard to FIG. 1. The server further stores reviewer feedback information 62 received from the communication device and related to image quality and/or other parameters noted by a reviewer of a coded medical image. Additionally, the server comprises a processor 64 that executes, and a memory or computer-readable medium 66 that stores computer executable instructions as described with regard to the processor 18 and memory 20 of FIG. 1. Similarly, the communication device 38 comprises a processor 68 that executes, and a memory or computer-readable medium 70 that stores, computer executable instructions as described with regard to the processor 18 and memory 20 of FIG. 1.

The communication device further comprises a user interface (UI) 72 via which the reviewer can interact with the communication device to view one or more coded medical images 60 received from the server, and which may be stored in memory 70, as well as to enter feedback for transmission to the server. An optical scanner 74 (e.g., a camera device on the communication device or the like) is also provided for scanning a unique code embedded in or appended to each coded medical image. A feedback application 76 is executed by the processor and accesses the scanning device, via which the reviewing physician or other authorized party can scan the embedded code during image review. The feedback application also includes a decoder module 78 that decodes the scanned code (e.g., a PR code, a barcode, etc.) and extracts information related to one or more of authorized recipient IP addresses or URLs to which the reviewer's feedback is to be transmitted, information related to imaging device parameters (e.g., imaging device type, make and model, last service date, year of manufacture, imaging device ID information, or any other information relevant to the image generated by the imaging device), validation information that ensures that the reviewer is authorized to review the coded image, or any other information encoded in the scanned unique coding.

The feedback application 76 also presents to the reviewer via the UI one or more feedback forms 80, which are retrieved form the server via a link included in the unique code for the image, and into which the reviewer can enter feedback on the image. The feedback forms are retrieved based on the information encoded in the unique code embedded in or appended to the image under review. For example, different forms for different imaging modalities, acquisition modes or diagnostic questions can be presented to the reviewer. The unique code also includes information related to the manner in which to relay the feedback information to relevant parties, such as a list of IP addresses or URLs of servers to which to send the entered feedback. Additionally or alternatively, the feedback recipients can be encoded by a profile ID included in the unique code, wherein the profile ID is linked to a list of approved recipients on the server 36.

The feedback application transmits the entered feedback to the server 36 for storage and transmission to relevant parties, such as the medical device manufacturer, the radiology institution from which the image originates, etc. Negative feedback can be used to identify design flaws, imaging devices in need of service, etc. In another embodiment, the feedback is transmitted directly from the communication device to the relevant parties' devices or servers. Feedback is transmitted via the communication device's data connection 82. In one embodiment, the feedback is transmitted using an encrypted data transmission protocol 84 and is independent of the network connectivity of the viewing platform.

The validity of feedback can be guaranteed by a validation module 86 that identifies pre-approved users of the feedback application (e.g., only registered physicians are approved, or the like). In one embodiment, pre-approved reviewers are white-listed for a specific image (e.g., the referring physician, the responsible radiologist, and/or other pre-approved parties). In another embodiment, feedback is filtered after receipt at the server 36 based on whether the reviewer has been approved, or based on other criteria.

Moreover, the unique code can also be scanned to collect feedback from image post-processing workstations, which are commonly used to further analyze acquired images, e.g. for organ segmentation, quantification, etc. In this way, information about the quality of image analysis methods can be collected as well. Additionally, the unique code may also comprise information about image quality measures which are calculated automatically upon image acquisition, such as signal to noise ratio, distortions or automated QA measures, etc., and this information can be fed back to the relevant parties using the feedback application as a transfer channel.

Figure 3:
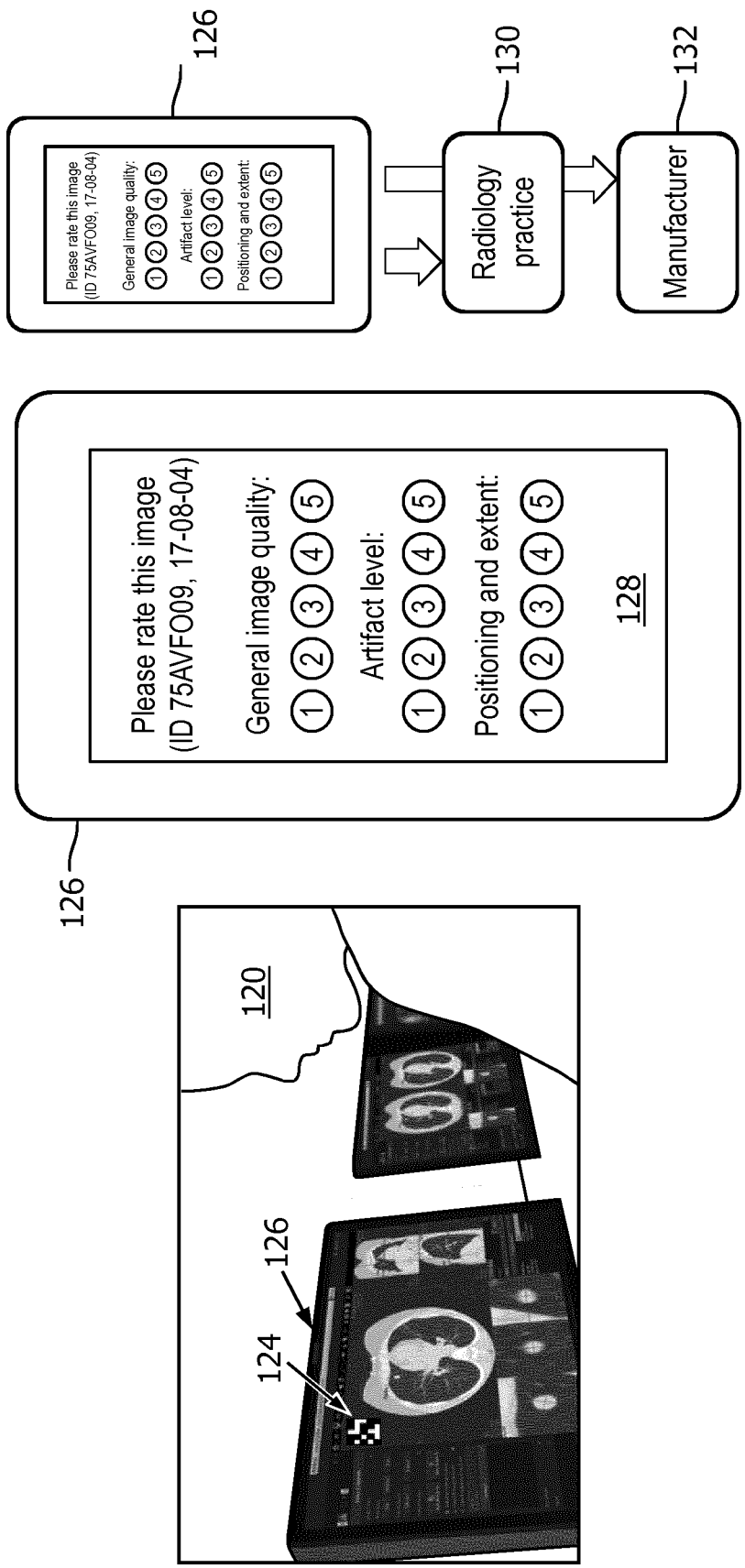
FIG. 3 is an illustration of the proposed concept, showing a reviewer viewing a coded image on a workstation, wherein the coded image includes a QR code.

FIG. 3 is an illustration of the proposed concept, showing a reviewer 120 viewing a coded image on a workstation 122, wherein the coded image includes a QR code 124 that was embedded in the image during acquisition and placed in an image area not containing diagnostic information. After scanning the code with the feedback app on the reviewer's smartphone 126, the physician is presented with a quality feedback form 128. The feedback is relayed from the smartphone 126 to the relevant data recipients, for example the radiology practice 130 that acquired the image and the medical device manufacturer 132.

The feedback form 128 in the example of FIG. 3 asks the reviewer to rate several features of the image, including general image quality, artifact level, and positioning and extent of the image. Additionally, the form identifies the image by device ID (i.e., the ID of the imaging device that captured the image) and date of acquisition. However, it will be understood by those of skill in the relevant arts that the image can be identified by any suitable identification features, and that the feedback form may include selectable ratings for any desired image features that may be rated by the reviewer. In another embodiment, the feedback form includes a selectable indicator by which the reviewer may accept or reject the image.

Figure 4:
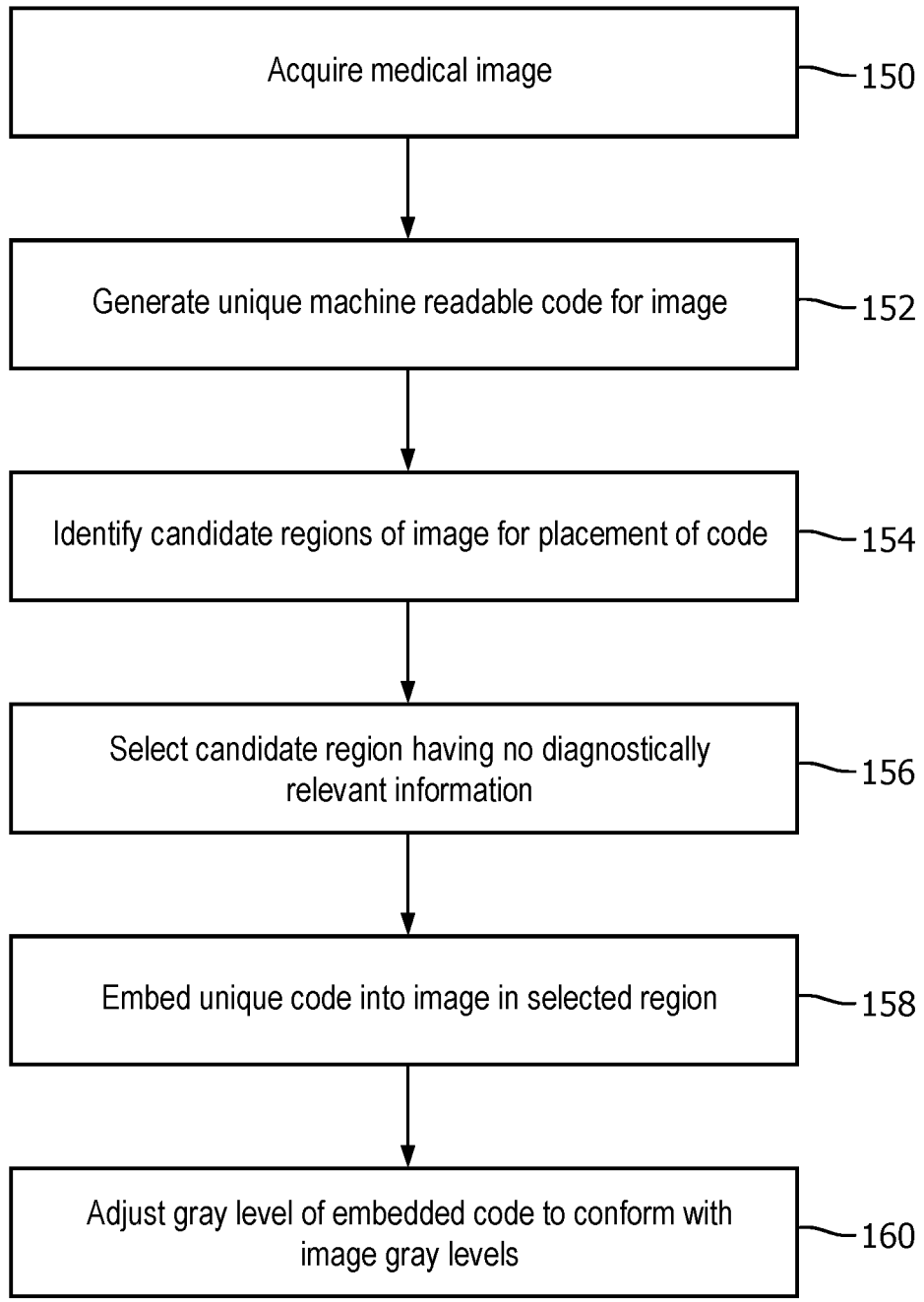
FIG. 4 illustrates a method for embedding a unique code into a medical image.

FIG. 4 illustrates a method for embedding a unique code into a medical image, wherein the unique code comprises information for directing a communication device that scans the unique code to a server that provides a feedback form to the communication device for reviewing the medical image. At 150, a medical image is acquired by a medical imaging device. The imaging device may be, for instance, a medical imaging device such as an x-ray device, a computed tomography (CT) device, a magnetic resonance imaging (MRI) device, a positron emission tomography (PET) device, a single-photon emission computed tomography (SPECT) device, or any other suitable imaging device. In another embodiment, the imaging device is a multi-modal imaging device that combines two or more of the foregoing imaging capabilities.

At 152, a unique machine-readable code, such as a QR code, a bar code, or a watermark or the like, is generated for each acquired medical image. The generated code can comprise information about the imaging device used to generate the image (e.g., device ID, manufacturer information such as model and serial number, acquisition parameters during the patient scan), as well as a unique identifier for the image. The unique code also comprises information (e.g., a link, IP address, URL, or the like) that directs a scanning device (e.g., a smartphone) used to scan the embedded code to a server that provides feedback forms to the smartphone for use by an image reviewer. In one embodiment, the embedded code is configured to omit personal, medical and/or patient information.

At 154, candidate regions of the acquired image are identified for placement of the unique coding so as not to obstruct the subject of the image. At 156, one of the candidate region that does not contain diagnostically relevant information (e.g., such as a region comprising air outside the patient) is selected for placement of the unique code. This can be achieved using, e.g., automatic segmentation of the patient outline. In one embodiment, diagnostically relevant areas of the image are automatically determined (e.g. based on automatic detection of organs linked to the scan request), and the unique code is embedded in the image where it is most likely to be seen during review. Although various described embodiments refer to a QR code, any other optically machine-readable code cable of representing readable information can be used.

In another embodiment, a new image layer is generated into which the unique code is embedded. The new image layer can be switched on or off for viewing by the reviewer of the image, or can be presented in separate series or snapshots in the dataset. For instance, additional image layer data comprising the unique code can be inserted into the image data in order to cause the image layer comprising the unique coding to be overlaid onto the image or to otherwise be presented after the reviewer views the image. During review, the reviewer of the image toggles the additional image layer on or off (e.g., on to view or scan the embedded coding, or off to view the unimpeded image), or selects an icon to view the appended unique coding.

At 158, the unique code is embedded into the selected candidate region of the image. At 160, a gray level adjustment is executed to adjust the pixel values of the embedded coding, such that the gray level values of the embedded code are set according to the gray level values of the diagnostically relevant image features. In one embodiment, the gray level of the embedded code is adjusted to match an average gray level for the image. In another embodiment, the gray level of the embedded code is adjusted to be brighter than an average gray level for the image by a predetermined percentage (e.g., 10%, 25%, or some other predetermined percentage), in order to ensure that the embedded code is easily viewable by the reviewer and/or a scanning device used to scan the code. In this manner, the embedded coding is easily readable in default level/window settings for the main diagnostic purpose because the gray levels of the embedded code do not substantially alter the overall image histogram. Coded images are transmitted to one or more servers for storage and access by a reviewer.

Figure 5:
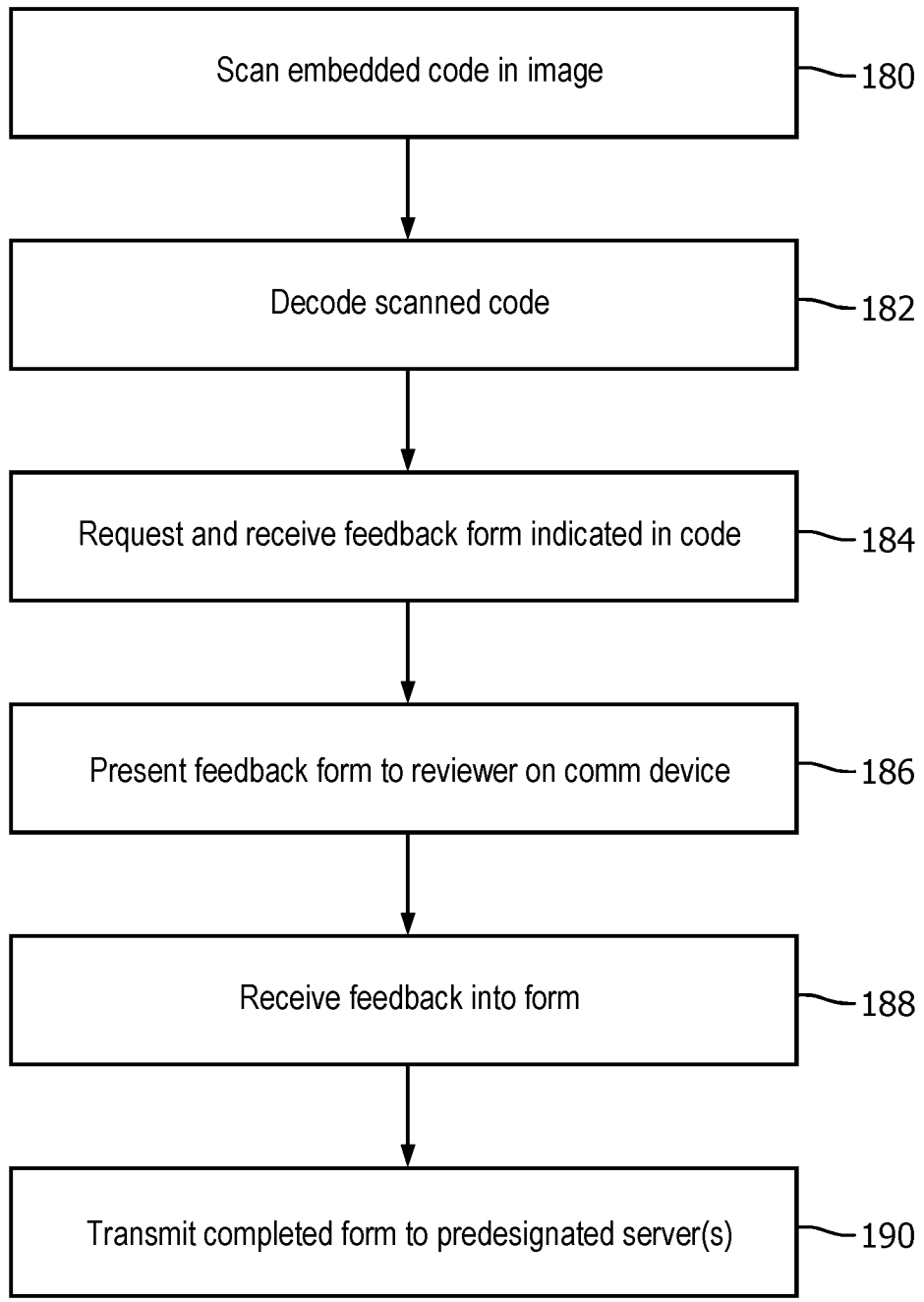
FIG. 5 illustrates a method for providing feedback on image quality based on information included in a unique coding embedding in a medical image under review, in accordance with various aspects described herein.

FIG. 5 illustrates a method for providing feedback on image quality based on information included in a unique coding embedding in a medical image under review, in accordance with various aspects described herein. At 180, a reviewer viewing a coded image employs a communication device (e.g., a smartphone, tablet, laptop, or the like) to scan the embedded code. At 182, a feedback application on the communication device receives and decodes the scanned code information, which includes information (a link, URL, IP address, etc.) for retrieving a feedback form for the coded image from the server. That is, the feedback application decodes the scanned code to read the information included therein in order to retrieve the feedback form and permit the reviewer to provide feedback to a server regarding image quality. Decoding of the scanned code can comprise extracting information related to one or more of authorized recipient IP addresses or URLs to which the reviewer's feedback is to be transmitted, information related to imaging device parameters (e.g., imaging device type, acquisition parameters used during the scan during which the image was acquired, make and model, last service date, year of manufacture, imaging device ID information, or any other information relevant to the image generated by the imaging device), validation information that ensures that the reviewer is authorized to review the coded image, or any other information encoded in the scanned unique coding.

At 184, a feedback form corresponding to the coded image under review is requested from the server via a link or IP address or a URL information included in the scanned code. At 186, the requested feedback form is presented to the reviewer on the communication device. At 188, feedback is received into the feedback form on the communication device. At 190, the completed feedback form is transmitted to one or more predesignated servers.

In one embodiment, the feedback application transmits the entered feedback to a server for storage and transmission to relevant parties, such as the medical device manufacturer, the radiology institution from which the image originates, etc. In another embodiment, the feedback is transmitted directly form the communication device to the relevant parties' devices or servers. Feedback is transmitted via the communication device's data connection. In one embodiment, the feedback is transmitted using an encrypted data transmission protocol and is independent of the network connectivity of the viewing platform.

The validity of feedback can be guaranteed identifying pre-approved users of the feedback application (e.g., only registered physicians are approved, or the like). In one embodiment, the IP addresses or URLs of preapproved users are included in the embedded code, such that a feedback application on a communication device that does not have a pre-approved status cannot decode the embedded code after scanning.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A system that facilitates determining medical image quality via a unique coding embedded in a medical image, comprising:
   a medical imaging device configured to acquire an image of a patient;
   a coding device comprising at least one electronic processor programmed to:
   generate a machine-readable unique code for an acquired image, wherein the unique code identifies the imaging device that acquired the image, at least one party authorized to review the acquired image, and at least one communication link for accessing and completing at least one feedback form related to the acquired image, wherein the unique code comprises a list of IP addresses or URLs of one or more servers to which the completed at least one feedback form is to be transmitted;
   associate the unique code with the acquired image such that the associated unique code is decodable when scanned; and
   adjust a gray level of the associated unique code to correspond to a gray level of the acquired image.

2. The system according to claim 1, wherein the at least one electronic processor is programmed to associates the unique code with the image by embedding the unique code into the image.

3. The system according to claim 2, wherein the at least one electronic processor is programmed to identify candidate regions of the image for insertion of the unique code.

4. The system according to claim 3, wherein the at least one electronic processor is programmed to select a candidate region of the image that is outside of a region of interest of the acquired image, and wherein the embedding component embeds the unique code into the selected candidate region.

5. The system according to claim 1, wherein the at least one electronic processor is programmed to:
generate a new image layer by inserting new image layer data into image data of the acquired image, and
inserts the unique code into the new image layer data.

6. The system according to claim 5, wherein the new image layer comprises a toggle function such that when the new image layer is toggled on the unique code is visible for scanning, and when the unique code is toggled off the unique code is hidden and a view of the acquired image is unimpeded.

7. The system according to claim 1, wherein the unique code comprises a quick response (QR) code.

8. A system for providing feedback indicative of image quality for an acquired medical image, comprising:
a server comprising a database of coded medical images, wherein each coded image comprises a machine-readable unique code including information related to an identity of a medical imaging device that acquired the coded image, an identity of at least one party authorized to review the coded image, and a link to at least one feedback form into which image quality feedback can be entered; and
a communication device comprising:
a scanner configured to scan the machine-readable unique code; and
a processor that executes a feedback application configured to:
decode the scanned code;
retrieve the at least one feedback form from the server via the link;
present the retrieved feedback form to a reviewer for completion; and
transmit the completed feedback form to the server;
wherein the unique code comprises a list of IP addresses or URLs of one or more servers to which the completed feedback is to be transmitted, and wherein the feedback application is configured to transmit the completed feedback form to all IP addresses or URLs in the list.

9. The system according to claim 8, wherein the feedback application is further configured to validate the identity of the reviewer by comparing an IP address or URL of the communication device to a list of pre-approved IP addresses or URLs permitted to review the coded image.

10. The system according to claim 8, wherein the unique code is a quick response (QR) code.

11. A method of determining medical image quality via a unique coding embedded in a medical image, comprising:
acquiring an image of region of interest in a patient via a medical imaging device; generating a machine-readable unique code for an acquired image, wherein the unique code identifies the imaging device that acquired the image, at least one party authorized to review the acquired image, and at least one communication link for accessing and completing at least one feedback form related to the acquired image;
associating the unique code with the acquired image such that the associated unique code is decodable when scanned; and adjusting a gray level of the associated unique code to correspond to a gray level of the acquired image, wherein the unique code comprises a list of IP addresses or URLs of one or more servers to which the completed at least one feedback form is to be transmitted; and
transmitting the completed feedback form to all IP addresses or URLs in the list of IP addresses or URLs.

12. A method for providing feedback indicative of image quality for an acquired medical image, comprising:
scanning a machine readable unique code in a coded medical image;
decoding the scanned code;
retrieving at least one feedback form from a server via a link presenting the retrieved feedback form to a reviewer for completion;
wherein the machine readable unique code comprises information related to an identity of a medical imaging device that acquired the coded image, an identity of at least one party authorized to review the coded image, and the link to the at least one feedback form into which image quality feedback can be entered and includes a list of IP addresses or URLs of one or more servers to which the completed feedback form is to be transmitted; and
transmitting the completed feedback form to all IP addresses or URLs in the list of IP addresses or URLs.

13. The method according to claim 12, further comprising validating the identity of the reviewer by comparing an IP address or URL of the communication device to a list of pre-approved IP addresses or URLs permitted to review the coded image.

* * * * *